(12) United States Patent
Smith et al.

(10) Patent No.: US 6,435,007 B1
(45) Date of Patent: Aug. 20, 2002

(54) MATERIALS BREAKTHROUGH MONITORING SENSOR SYSTEM

(75) Inventors: Dean Smith, Dover Foxcroft; Todd Mlsna, Orono; Jeremy Hammond, Hampden, all of ME (US)

(73) Assignee: Sensor Research & Development Corporation, Orono, ME (US)

( * ) Notice: Subject to any disclaimer, the term of this patent is extended or adjusted under 35 U.S.C. 154(b) by 0 days.

(21) Appl. No.: 09/560,578

(22) Filed: Apr. 27, 2000

Related U.S. Application Data

(60) Provisional application No. 60/133,058, filed on May 6, 1999.

(51) Int. Cl.$^7$ ............................................. G01N 15/08
(52) U.S. Cl. ........................................ 73/38; 73/31.05
(58) Field of Search .................. 73/24.01, 24.06, 73/38, 31.05, 31.06, 64.47

(56) References Cited

U.S. PATENT DOCUMENTS

| | | | |
|---|---|---|---|
| 3,498,110 A | * 3/1970 | Brun | 73/38 |
| 3,590,634 A | * 7/1971 | Pasternak et al. | 73/38 |
| 3,926,561 A | * 12/1975 | Lucero | 73/23.35 |
| 3,933,433 A | 1/1976 | Hooker | |
| 4,374,090 A | 2/1983 | McClure | |
| 4,443,791 A | 4/1984 | Risgin | |
| 4,457,161 A | 7/1984 | Iwanaga et al. | 340/634 |
| 4,670,405 A | 6/1987 | Stetter et al. | 422/28 |
| 5,012,668 A | 5/1991 | Haworth | 73/24 |
| 5,025,653 A | 6/1991 | Schuldt | |
| 5,047,352 A | 9/1991 | Stetter et al. | |
| 5,076,094 A | 12/1991 | Frye et al. | 73/11.03 |
| 5,184,500 A | 2/1993 | Krcma et al. | |
| 5,235,235 A | 8/1993 | Martin et al. | |
| 5,493,730 A | 2/1996 | Vo-Dinh | 436/104 |
| 5,550,062 A | 8/1996 | Wohltjen et al. | 436/92 |
| 5,659,130 A | 8/1997 | Chung et al. | 73/64.47 |
| 5,763,283 A | 6/1998 | Cernosek et al. | |
| 5,801,297 A | * 9/1998 | Misfud et al. | 73/23.34 |
| 5,837,888 A | * 11/1998 | Mayer et al. | 73/38 |
| 5,948,962 A | 9/1999 | Matthiessen | |
| 5,992,215 A | * 11/1999 | Caron et al. | 73/24.01 |

FOREIGN PATENT DOCUMENTS

| | | | | |
|---|---|---|---|---|
| SU | 1631363 | * | 2/1991 | 73/38 |

OTHER PUBLICATIONS

Designation D 1776–98; "Standard Practice for Conditioning and Testing Textiles" American Society for Testing and materials, West Conshohocken, PA, 19428, reprinted from the Annual Book of ASTM Standards, Copyright ASTM.

Designation F1194–99; "Standard Guide for Documenting the Results of Chemical Permeation Testing of Materials Used in Protective Clothing", American Society for Testing and materials, West Conshohocken, PA, 19428, reprinted from the Annual Book of ASTM Standards, Copyright ASTM.

(List continued on next page.)

*Primary Examiner*—Daniel S. Larkin
(74) *Attorney, Agent, or Firm*—Pierce Atwood

(57) ABSTRACT

A sensor system that monitors agent breakthrough through a vapor barrier and related test process. The system includes a substantially airtight test chamber for retaining the vapor barrier, which may be formed of one or more layers of one or more materials. A sensor element array placed adjacent to the barrier under test includes elements that are sensitive to one or more agents of interest and elements that are insensitive to such agents. The insensitive elements provide a baseline reference signal that is compared to the output signal of the sensitive elements. As the agent contacts the array, the electrical signal output from the sensitive elements changes in comparison to that of the reference elements. The sensor array is sensitive enough to detect low levels of the agent when the agent passes through the barrier. A control system is used to regulate and monitor environmental conditions within the chamber and to process electrical signals from the sensor array.

17 Claims, 2 Drawing Sheets

OTHER PUBLICATIONS

Designation: F1186–99; "Standard Classification System for Chemicals According to Functional Groups", American Society for Testing and materials, West Conshohocken, PA, 19428, reprinted from the Annual Book of ASTM Standards, Copyright ASTM.

Designation: F1001–99a; "Standard Guide for Selection of Chemicals to Evaluate Protective Clothing Materials" American Society for Testing and materials, West Conshohocken, PA, 19428, reprinted from the Annual Book of ASTM Standards, Copyright ASTM.

Designation F739–99a; "Standard Test Method for Resistance of Protective Clothing Materials to Permeation by Liquids or Gases Under Conditions of Continuous Contact", American Society for Testing and materials, West Conshohocken, PA, 19428, reprinted from the Annual Book of ASTM Standards, Copyright ASTM.

F903–99a; "Standard Test Method for Resistance of Materials Used in Protective Clothing to Penetration by Liquids", American Society for Testing and materials, West Conshohocken, PA, 19428, reprinted from the Annual Book of ASTM Standards, Copyright ASTM.

* cited by examiner

Fig. 1 (Prior Art)

MATERIALS BREAKTHROUGH MONITORING SENSOR SYSTEM

CROSS REFERENCE TO RELATED PATENT APPLICATION

This application claims the priority benefit of U.S. provisional application Serial No. 60/133,058, filed May 6, 1999, of the same title for the same inventors. The content of the related patent application is incorporated herein by reference.

This invention was made with U.S. government support under contract no. N000-14-98-0394 awarded by DoD—Office of Naval Research. The U.S. government may have certain rights in the invention.

BACKGROUND OF THE INVENTION

1. Field of the Invention

The present invention relates to a sensor system that monitors agent breakthrough that occurs through what is otherwise intended to be a chemical barrier. This system detects and quantifies the occurrence of chemical breakthrough through a variety of analyte materials. Specific example applications include chemical suit materials and filter beds against chemical warfare agents. Military field deployments of this system can be imagined as well in the form of sensors in gas mask filter canisters. These "smart gas masks" may indicate imminent defeat of the mask as well as an all clear to indicate that it is safe to remove the mask again.

2. Description of the Prior Art

The most common system currently available for this detection purpose is a system designed to monitor fabric breakthrough using an impinger system as illustrated in a simplified view in FIG. 1. A piece of fabric is placed in a chamber so that it creates a seal. Carrier gas flows through the fabric when a pressure differential is created by a vacuum pump. A few drops of agent are placed on a piece of fabric. The agent eventually moves its way through the fabric carried by the carrier gas, where it is collected by mixing with a suitable solvent. A sample of the solvent is collected periodically and from the concentration of the agent in the solvent a breakthrough time can be calculated.

What is needed is a system that takes the guesswork out of the prior system and related technique by providing real time feedback on agent breakthrough.

SUMMARY OF THE INVENTION

The present invention is an agent breakthrough monitoring system that provides real-time feedback of when agent breakthrough occurs. The system operates around the performance of arrays of sensitive chemi-resistive semiconducting metal oxide (SMO) and/or polymer films. These films serve as the transduction media for the resistive and surface acoustic wave (SAW) sensor platforms. As the chemical compound that the material is being tested against breaks through the test material, it passes over the sensor elements in the array, resulting in changes in resistance (for the SMO sensors) and changes in frequency (for the polymer coated SAW sensors). The signatures from these changes will provide the information necessary to determine exposure levels as a function of time. Other types of suitable sensors include chemical field effect transistors, surface Plasmon resonance arrays, conducting polymer arrays, chemical hybrid sensor arrays, or any combination thereof. Such sensors must be reactive to changes in their surface conditions such that electrical signal outputs change with surface condition changes.

These and other advantages of the present invention will become apparent upon review of the following detailed description, the accompanying drawings, and the appended claims.

BRIEF DESCRIPTION OF THE DRAWINGS

Figure 1:
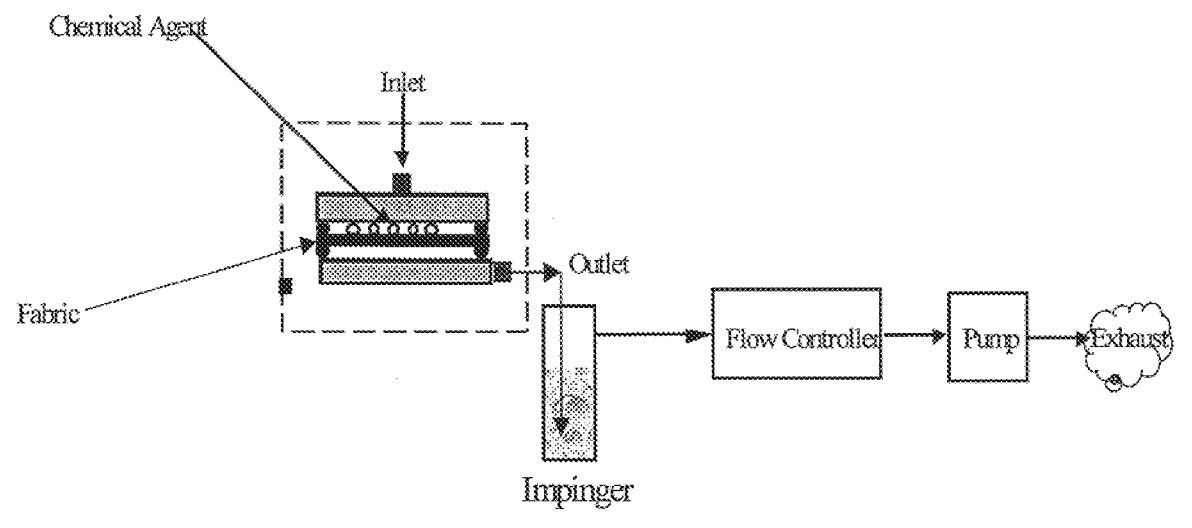

FIG. 1 is a simplified diagrammatic representation of the vapor barrier analysis system of the prior art.

DETAILED DESCRIPTION OF THE PREFERRED EMBODIMENT

Figure 2:
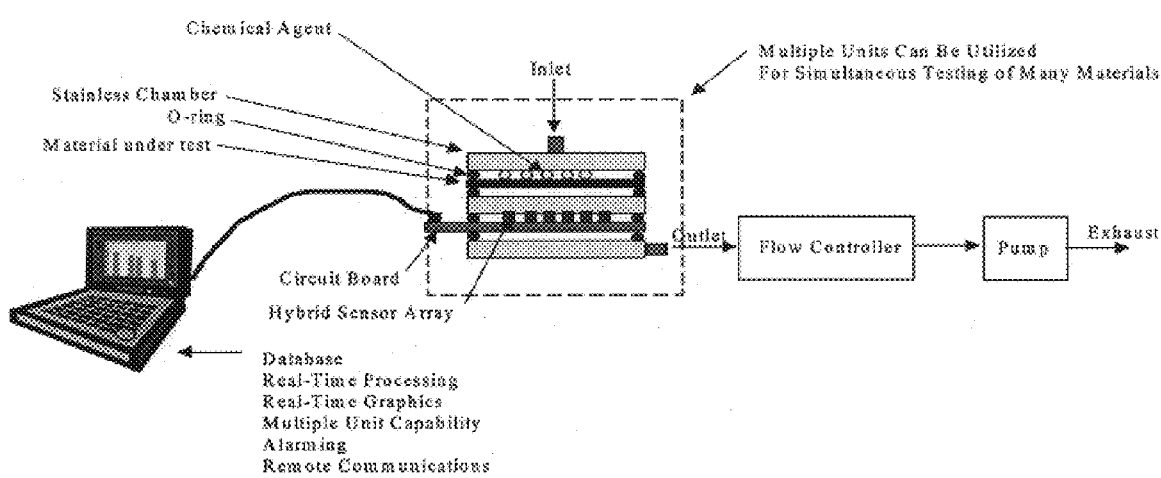
FIG. 2 is a simplified diagrammatic representation of the vapor barrier analysis system of the present invention.

The present sensor system designed to overcome the limitations associated with the prior existing systems is described in combination with the illustration of FIG. 2.

The object of the system is to be able to identify and quantify the breakthrough of chemicals through analyte materials. To do this, a substantially airtight test chamber is used. The chamber is preferably made out of stainless material and includes three pieces. The top piece is designed to accommodate the placement of the chemical onto the barrier material-under-test and provide the inlet for the carrier gas. The barrier material-under-test is positioned between the top piece and the middle piece of the chamber. In order to maintain a substantially airtight system, O-rings are placed on either side of the material. A circuit board that contains the sensor array and associated electronics for temperature control, sensor operation, and signal measurements is positioned between the middle piece and the bottom piece. O-rings are preferably used between these interfaces as well. The bottom piece provides the exhaust for the chamber as well. Gas flow is controlled via the flow controller and the pump source. Chamber control/feedback and data from one chamber, or multiple chambers, is linked to a computer. The computer has the ability to:

1) control the operating temperature of each sensor
2) provide a real-time, time synchronized database from each sensor element from each chamber
3) provide real-time graphics from any sensor/chamber (i.e. response/instantaneous concentration/cumulative concentration/etc. vs. time)
4) provide instantaneous and cumulative chemical exposure levels from each sensor/chamber
5) provide alarms and other event controls
6) allow remote monitoring and communication
7) allow unmanned experimentation
8) other selectable operations of interest.

The flow through the system during fabric testing involves the following process steps. First, a few drops of the chemical to be tested are placed on an initial agent-contact surface of the fabric or other barrier material to be evaluated. The pump and the flow controller maintain constant flow of the chemical's vapor through the entire test configuration. A carrier gas such as, but not limited to, dry air or nitrogen, is directed into the system at the inlet and flows into the top portion of the test chamber unit where it interfaces with the fabric and the drops of test chemical whose break through the fabric is to be monitored. It is to be noted that the barrier may be formed of one or more layers of one or more materials that may be evaluated. The carrier gas flows through the air-permeable material and then passes over the sensor array. The array of sensors includes one or more active sensors that are sensitive to chemical agents and one or more reference sensors that are insensitive to chemical agents. As the chemical begins to break through the material to the exiting surface of that material, the sensors react with the directed chemical vapor and respond by changing resistance (for the SMO sensors) and oscillation frequency (for the polymer-coated SAW sensors). These changes are transformed into electrical signatures via electronics and then fed to the computer where they can be processed, displayed, stored, etc. Alternative sensor arrangements may be employed including, but not limited to, chemical field effect transistors, surface Plasmon resonance arrays, conducting polymer arrays, chemical hybrid sensor arrays, or any combination thereof.

The sensor array is designed to perform well over a wide range of concentrations as determined, by example, through time weighted average (TWA) to immediate danger to health level (IDHL). The specific operation of a suitable SAW sensor array is described in U.S. Pat. No. 5,992,215 entitled "Surface Acoustic Wave Mercury Vapor Sensors" assigned to a common assignee. The content of that patent is incorporated herein by reference with regard to the description of the set up and signal processing associated with SAW sensors and that can relatedly be applied to the configuration of, and processing of signals from, the other types of sensors noted herein.

It should be understood that the embodiments mentioned here are merely illustrative of the present invention. Numerous design modifications and variations in use of the invention may be contemplated in view of the following claims without straying from the intended scope of the invention herein disclosed.

What is claimed is:

1. A test system to evaluate the breakthrough resistance to chemical agents of a vapor barrier having an initial agent-contact surface and an exiting surface, said system comprising:
   a test chamber including a carrier gas inlet and a carrier gas outlet arranged to provide a carrier gas stream through said test chamber;
   means for retaining said vapor barrier within said test chamber so that said carrier gas stream flows through said vapor barrier with said agent-contact surface facing upstream and said exiting surface facing downstream;
   an array of sensors positioned downstream of said vapor barrier, wherein said sensors generate signals that change when said sensors detect an agent; and
   means for generating breakthrough resistance characteristics of said vapor barrier in response to signals received from said sensors.

2. The test system as claimed in claim 1 wherein said vapor barrier is formed of one or more vapor barrier materials.

3. The test system as claimed in claim 1 wherein said sensors are selected from the group consisting of chemiresistive SMO sensor arrays, SAW sensor arrays, chemical field effect transistors, surface Plasmon resonance arrays, conducting polymer arrays, chemical hybrid sensor arrays, or any combination thereof.

4. The test system as claimed in claim 1 further comprising means to control environmental conditions at the initial surface of said vapor barrier.

5. The test system as claimed in claim 4 wherein said array of sensors provides a means to monitor environmental conditions within said test chamber.

6. The test system as claimed in claim 1 wherein said array of sensors includes one or more active sensors that are sensitive to said agent and one or more reference sensors that are insensitive to said agent.

7. The test system as claimed in claim 1 wherein said test chamber includes first, second, and third pieces, said vapor barrier being retained between said first and second pieces and said array of sensors being positioned between said second and third pieces.

8. The test system as claimed in claim 7 further comprising one or more seals positioned between said first and second pieces.

9. The test system as claimed in claim 7 further comprising one or more seals positioned between said second and third pieces.

10. A process for evaluating the breakthrough resistance to chemical agents of a vapor barrier having an initial agent-contact surface and an exiting surface, said process comprising:
    providing a test chamber including a carrier gas inlet and a carrier gas outlet arranged to provide a carrier gas stream through said test chamber;
    placing said vapor barrier within said test chamber so that said carrier gas stream flows through said vapor barrier with said agent-contact surface facing upstream and said exiting surface facing downstream;
    placing an array of sensors downstream of said vapor barrier, wherein said sensors generate signals that change when said sensors detect an agent;
    placing an agent on said agent-contact surface; and
    monitoring signals generated by said sensors to detect passage of said agent from said agent-contact surface to said exiting surface.

11. The process as claimed in claim 10 wherein said array of sensors includes one or more active sensors that are sensitive to said agent and one or more reference sensors that are insensitive to said agent.

12. The process as claimed in claim 10 wherein monitoring signals includes coupling said sensors to a controller, wherein said controller is programmed to process properties of said signals to detect a change therein.

13. The process as claimed in claim 12 wherein said controller is programmed to generate instantaneous and cumulative exposure levels of said agent passing through said vapor barrier.

14. The process as claimed in claim 10 wherein said sensors are selected from the group consisting of chemiresistive SMO sensor arrays, SAW sensor arrays, chemical field effect transistors, surface Plasmon resonance arrays, conducting polymer arrays, chemical hybrid sensor arrays, or any combination thereof.

15. The process as claimed in claim 10 further comprising regulating and monitoring environmental conditions within said test chamber.

16. The process as claimed in claim 15 wherein monitoring environmental conditions includes evaluating environment-related signals from said sensors.

17. The process as claimed in claim 10 wherein said vapor barrier is formed of one or more layers of vapor barrier materials.

* * * * *